United States Patent [19]

Tessier et al.

[11] Patent Number: 4,689,342

[45] Date of Patent: * Aug. 25, 1987

[54] CERTAIN INSECTICIDAL CYCLOPROPANE CARBOXYLIC ACID DERIVATIVES

[75] Inventors: Jean Tessier, Vincennes; Jean-Pierre Demoute, Montreuil-Sous-Bois, both of France

[73] Assignee: Roussel Uclaf, Paris, France

[*] Notice: The portion of the term of this patent subsequent to Sep. 17, 2002 has been disclaimed.

[21] Appl. No.: 554,092

[22] Filed: Nov. 21, 1983

[30] Foreign Application Priority Data

Nov. 25, 1982 [FR] France ................................ 82 19761

[51] Int. Cl.$^4$ ................ C07D 207/327; C07C 121/46; C07C 69/743; A01N 53/00
[52] U.S. Cl. .................................... 524/427; 514/521; 514/531; 546/281; 546/300; 546/302; 548/561; 548/562; 560/124; 558/255; 558/257; 558/407
[58] Field of Search ........................ 260/465 D, 455 R; 560/124; 546/300, 281; 548/561, 562, 560; 558/255, 257, 407; 514/427, 521, 531

[56] References Cited

U.S. PATENT DOCUMENTS 4,542,142 9/1985 Martel et al. ........................ 514/345

Primary Examiner—Alan L. Rotman
Attorney, Agent, or Firm—Bierman and Muserlian

[57] ABSTRACT

Novel esters in all possible isomeric forms or a mixture thereof having the formula

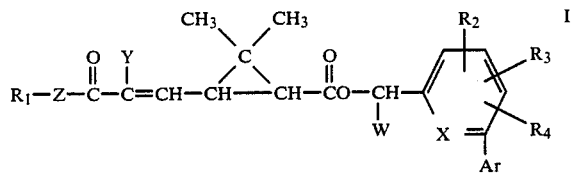

wherein Y is selected from the group consisting of hydrogen, halogen, —OAlK and

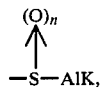

AlK is alkyl of 1 to 6 carbon atoms, n is 0, 1 or 2, Z is selected from the group consisting of —O— and —S—, $R_1$ is selected from the group consisting of (a) optionally unsaturated alkyl of 1 to 8 carbon atoms and optionally unsaturated cycloalkyl or cycloalkylalkyl of 3 to 8 carbon atoms optionally substituted with at least one member of the group consisting of halogen, —OH, —SH, —OR', —SR',

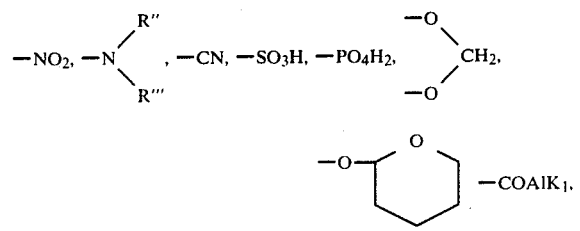

—SO$_2$AlK$_2$, —SO$_3$AlK$_3$, aryl optionally substtuted with at least one member of the group consisting of —OH, alkoxy of 1 to 8 carbon atoms, alkyl of 1 to 8 carbon atoms, halogen, —CF$_3$, —OCF$_3$, —SCF$_3$ and

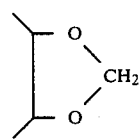

R' is alkyl of 1 to 8 carbon atoms, R" and R''' are individually selected from the group consisting of hydrogen and alkyl of 1 to 8 carbon atoms, AlK$_1$, AlK$_2$ and AlK$_3$ are individually alkyl of 1 to 18 carbon atoms (b) aryl of 6 to 14 carbon atoms optionally substituted with at least one substituent selected from the group consisting of —OH, alkoxy of 1 to 8 carbon atoms, alkyl of 1 to 8 carbon atoms, halogen, —OCF$_3$, —CF$_3$ and —SCF$_3$ and (c) heterocycle optionally substituted with at least one member of the group consisting of —OH, alkoxy of 1 to 8 carbon atoms, alkyl of 1 to 8 carbon atoms, halogen, —CF$_3$, —OCF$_3$ and —SCF$_3$, $R_2$, $R_3$ and $R_4$ are individually selected from the group consisting of hydrogen, halogen, alkyl of 1 to 8 carbon atoms, haloalkyl of 1 to 8 carbon atoms containing a plurality of halogens and alkoxy of 1 to 8 carbon atoms, W is selected from the group consisting of hydrogen and —CN, X is selected from the group consisting of carbon and nitrogen, Ar is selected from the group consisting of optionally substituted phenyl, pyridyl, thienyl, naphthyl, furyl and pyrrolyl and the ethylenic double bond may have Z or E geometry having parasitic activity, especially insecticidal, acaricidal and nematocidal activity.

37 Claims, No Drawings

CERTAIN INSECTICIDAL CYCLOPROPANE CARBOXYLIC ACID DERIVATIVES

STATE OF THE ART

Certain derivatives of cyclopropane carboxylic acid derivatives are known having in the 3-position the group ROOC—CH=CH— having essentially E geometry. Examples of such prior art are French Pat. Nos. 2,185,612, 2,418,218 and 2,143,820 as well as J. Chem. Soc., Perkin I (1974), p. 2470 and Pest. Sci., Vol. 7 (1976), p. 499. Copending U.S. patent applications Ser. No. 266,164 filed May 22, 1981, Ser. No. 296,076 filed June 30, 1981, Ser. No. 306,780 filed Sept. 29, 1981, Ser. No. 495,481 filed May 17, 1983 and U.S. Pat. No. 4,402,972, European Patent application No. EP 49.977 and International application No. WO 82/01368 describe related cyclopropane carboxylic acid derivatives.

OBJECTS OF THE INVENTION

It is an object of the invention to provide the novel Z and E isomers of the compounds of formula I as well as a novel process and novel intermediates for their preparation.

It is another object of the invention to provide novel pesticidal compositions and a novel method of killing insects and acariens.

It is a further object of the invention to provide novel compositions and method of combatting scabies and to provide anthelmintic activity.

These and other objects and advantages of the invention will become obvious from the following detailed description.

THE INVENTION

The novel compounds of the invention are esters in all possible isomeric forms or a mixture thereof having the formula

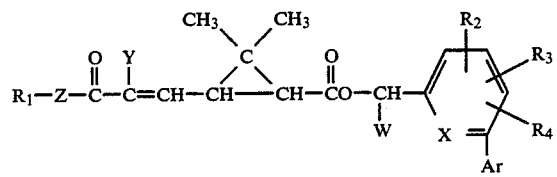

wherein Y is selected from the group consisting of hydrogen, halogen, —OAlK and

AlK is alkyl of 1 to 6 carbon atoms, n is 0, 1 or 2, Z is selected from the group consisting of —O— and —S—, $R_1$ is selected from the group consisting of (a) optionally unsaturated alkyl of 1 to 8 carbon atoms and optionally unsaturated cycloalkyl or cycloalkylalkyl of 3 to 8 carbon atoms optionally substituted with at least one member of the group consisting of halogen, —OH, —SH, —OR', —SR',

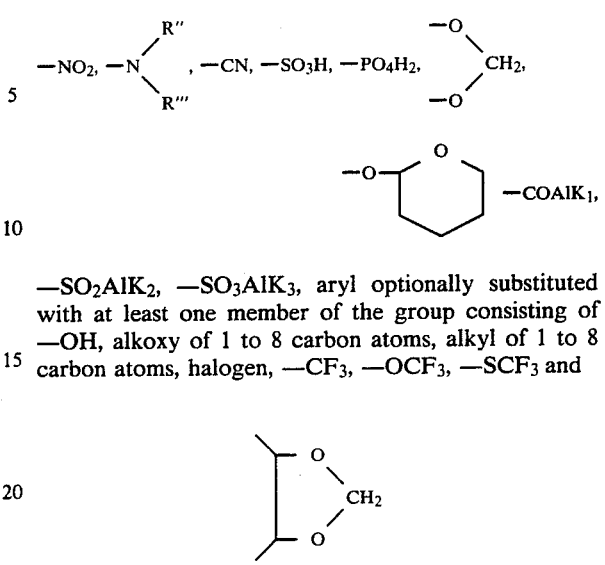

—SO$_2$AlK$_2$, —SO$_3$AlK$_3$, aryl optionally substituted with at least one member of the group consisting of —OH, alkoxy of 1 to 8 carbon atoms, alkyl of 1 to 8 carbon atoms, halogen, —CF$_3$, —OCF$_3$, —SCF$_3$ and

R' is alkyl of 1 to 8 carbon atoms, R" and R''' are individually selected from the group consisting of hydrogen and alkyl of 1 to 8 carbon atoms, AlK$_1$, AlK$_2$ and AlK$_3$ are individually alkyl of 1 to 18 carbon atoms (b) aryl of 6 to 14 carbon atoms optionally substituted with at least one substituent selected from the group consisting of —OH, alkoxy of 1 to 8 carbon atoms, alkyl of 1 to 8 carbon atoms, halogen, —OCF$_3$, —CF$_3$ and —SCF$_3$ and (c) heterocycle optionally substituted with at least one member of the group consisting of —OH, alkoxy of 1 to 8 carbon atoms, alkyl of 1 to 8 carbon atoms, halogen, —CF$_3$, —OCF$_3$ and SCF$_3$, $R_2$, $R_3$ and $R_4$ are individually selected from the group consisting of hydrogen, halogen, alkyl of 1 to 8 carbon atoms, haloalkyl of 1 to 8 carbon atoms containing a plurality of halogens and alkoxy of 1 to 8 carbon atoms, W is selected from the group consisting of hydrogen and —CN, X is selected from the group consisting of carbon and nitrogen, Ar is selected from the group consisting of optionally substituted phenyl, pyridyl, thienyl, naphthyl, furyl and pyrrolyl and the ethylenic double bond may have Z or E geometry.

The compounds of formula I exist in isomeric forms due to the presence of asymmetric carbon atoms in the 1- and 3-positions of the ring, to other asymmetric centers in the alcohol portions thereof and to the configuration of the double bond in the side chain in the 3-position as well as possible asymmetric centers in the $R_1$ substituents and the possible E and Z isomers.

Examples of Y are hydrogen, halogen such as fluorine, bromine or chlorine and AlK may be methyl, ethyl, n-propyl, isopropyl, n-butyl or branched butyl.

When $R_1$ is saturated alkyl, it is preferably methyl, ethyl, isopropyl, n-propyl, n-butyl, sec.-butyl, isobutyl, n-pentyl, n-hexyl, tert.-butyl, tert.-pentyl or neopentyl. When R is cycloalkyl, it is preferably cyclopropyl, cyclobutyl, cyclopentyl or cyclohexyl. When $R_1$ is cycloalkylalkyl optionally substituted with at least one alkyl, it is preferably one of the above saturated alkyls substituted by cyclopropyl, cyclobutyl, cyclopentyl or cyclohexyl such as 1-methyl-cyclobutyl, 1-methyl-cyclopentyl, 1-methyl-cyclohexyl or 2,2,3,3-tetramethyl-cyclopropyl.

When $R_1$ is an unsaturated alkyl, it is preferably an ethylenic group such as vinyl or 1,1-dimethyl-allyl or an acetylenic group such as ethynyl or propynyl.

Examples of $R_1$ as alkyl substituted with one or more functional groups are preferably alkyl of 1 to 8 carbon atoms such as methyl, ethyl, propyl, isopropyl, n-butyl, isobutyl or tert.-butyl substituted with at least one member of the group consisting of halogen, —OH, —SH, —OR' and —SR' and R' is selected from the group consisting of alkyl of 1 to 8 carbon atoms, —NO$_2$, —CN, —SO$_3$H, —PO$_4$H$_2$,

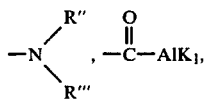

—SO$_2$AlK$_2$ and —SO$_3$AlK$_3$, R" and R''' are individually selected from the group consisting of hydrogen and alkyl of 1 to 8 carbon atoms and AlK$_1$, AlK$_2$ and AlK$_3$ are alkyl of 1 to 18 carbon atoms.

$R_1$ may also be alkyl substituted with an aryl group such as benzyl or phenethyl optionally substituted with at least one member of the group consisting of —OH, alkyl and alkoxy of 1 to 8 carbon atoms, halogen, —CF$_3$, —OCF$_3$, —SCF$_3$ and

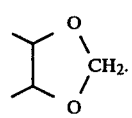 (G)

$R_1$ may also be alkyl substituted on two adjacent carbon atoms with the group

 (G$_1$)

or substituted with

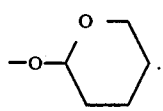

When $R_1$ is an alkyl radical substituted by one or more functional groups, the preferred examples of $R_1$ are (1) —(CH$_2$)$_{n1}$—CHal$_3$ wherein $n_1$ is an integer from 1 to 8 and Hal is a halogen, such as —CH$_2$—CCl$_3$, —CH$_2$—CF$_3$, —CH$_2$—CH$_2$—CCl$_3$ or —CH$_2$—CH$_2$—CF$_3$, (2) —(CH$_2$)$_{n2}$—CHHal$_2$ wherein $n_2$ is 0 to 8 and Hal is halogen such as —CH$_2$—CHCl$_2$, —CH$_2$—CHF$_2$ and —CHF$_2$, (3) —(CH$_2$)$_{n2}$—CH$_2$Hal wherein Hal and $n_2$ have the above definitions, such as —CH$_2$—CH$_2$—Cl or —CH$_2$—CH$_2$F, (4) —C≡(CHal$_3$)$_3$ wherein Hal is a halogen, such as —C(CF$_3$)$_3$ or

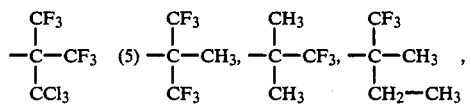

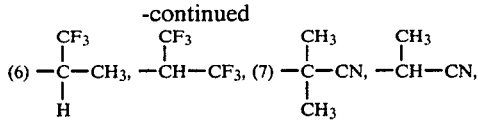

—(CH$_2$)$_{n1}$—CN wherein $n_1$ is 1 to 8,

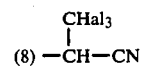

wherein Hal is a halogen, such as

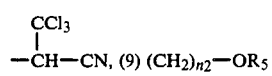

wherein $n_2$ has the above definition and $R_5$ is hydrogen or branched or linear alkyl of 1 to 8 carbon atoms such as —CH$_2$—OCH$_3$, —CH$_2$—CH$_2$—OCH$_3$, —CH$_2$CH$_2$—O—CH$_2$—CH$_3$ or —CH$_2$—CH$_2$—OH,

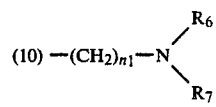

wherein $n_1$ is 1 to 8 and $R_6$ and $R_7$ are individually hydrogen or branched or linear alkyl of 1 to 8 carbon atoms such as —CH$_2$—CH$_2$—NH—CH$_3$,

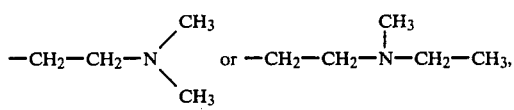

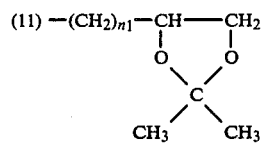

wherein $n_1$ is 1 to 8 such as

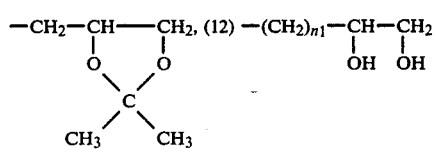

wherein $n_1$ is 1 to 8 such as

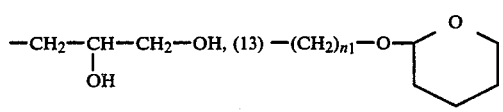

wherein n is 1 to 8 such as

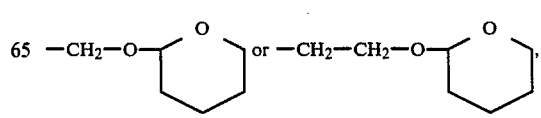

(14) —(CH$_2$)$_{n1}$— 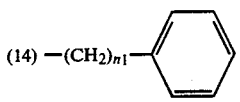

wherein n$_1$ is 1 to 8 such as benzyl or phenethyl and

(15) —(CH$_2$)$_{n1}$— 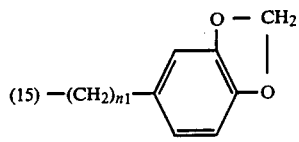

wherein n is 1 to 8 such as

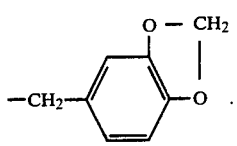

When R$_1$ is an optionally substituted aryl, preferred examples are phenyl optionally substituted with at least one member of the group consisting of —OH, alkyl and alkoxy of 1 to 8 carbon atoms, halogen, —CF$_3$, —OCF$_3$ and —SCF$_3$. Examples of R$_1$ as heterocycles are pyridinyl, furanyl, thiophenyl, oxazolyl and thiazolyl. The preferred halogens are fluorine, chlorine or bromine.

When R$_2$, R$_3$ and R$_4$ are alkyl, haloalkyl, halogen or alkoxy, they are preferably selected from the group consisting of methyl, ethyl, —CF$_3$, —CH$_2$—CF$_3$, fluorine, chlorine, bromine, methoxy, ethoxy or propoxy.

When Ar is a substituted aryl, it is preferably an aryl substituted with at least one member of the group consisting of halogen, haloalkyl of 1 to 8 carbon atoms and alkyl and alkoxy of 1 to 8 carbon atoms. Examples of substituted aryl are aryl substituted with at least one member of the group consisting of fluorine, chlorine, bromine, —CF$_3$, methyl and methoxy.

The compounds of formula I preferably contain the 1R, cis structure in the cyclopropane carboxylic moiety.

Among the preferred compounds of the invention of formula I are those wherein Y is hydrogen or halogen, those wherein R$_2$, R$_3$ are the same, those wherein W is hydrogen, those wherein X is a carbon atom, those wherein Ar is pyrrolyl or phenyl and those wherein R$_2$, R$_3$ and R$_4$ are alkyl of 1 to 4 carbon atoms such as methyl.

Among the preferred compounds of formula I are those wherein R$_3$ and R$_4$ are hydrogen and those wherein Y is hydrogen or fluorine and those wherein Z is —O—, especially those of the formula

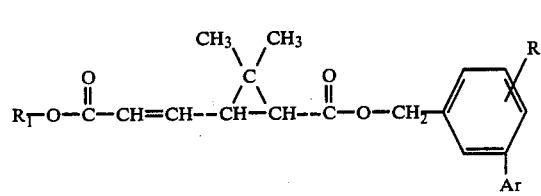

wherein R$_1$, R$_2$ and Ar have the above definitions, the geometry of the double bond is Z and the cyclopropane moiety has the 1R, cis structure.

The novel process of the invention for the preparation of the compounds of formula I comprises reacting an acid of the formula

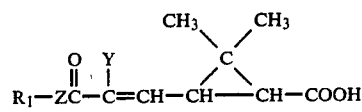

or a functional derivative thereof wherein R$_1$, Z and Y have the above definitions with an alcohol of the formula

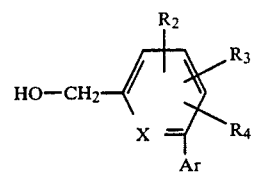

wherein R$_2$, R$_3$, R$_4$, Ar and X have the above definitions. The esterification reaction is preferably effected in the presence of a tertiary base such as pyridine or 4-dimethylamino-pyridine and dicyclohexylcarbodiimide.

Certain of the acids of formula II may be prepared by the processes described in European patent applications No. 0038271, No. 0041021, No. 0048186 and No. 0050534, for example.

The acids of formula II wherein Z is sulfur may be prepared by reacting an acid of the formula

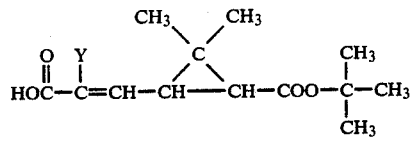

with a mercaptan of the formula R$_1$—SH in an organic solvent in the presence of dicyclohexylcarbodiimide and the resulting ester is saponified to remove the tert.-butyl ester group.

The acids of formula II wherein Y is —OAlK or

may be prepared by reacting a compound of the formula

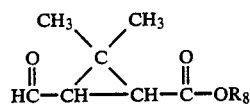

wherein R$_8$ is hydrogen or an easily cleavable ester with a compound of the formula

Y$_1$—CH$_2$—COOR$_1$ wherein $Y_1$ has the above Y definition and $R_1$ has the above definition and then hydrolyzing the easily cleavable ester if necessary.

The alcohols of formula III are generally known and may be prepared by the processes described in European patent application No. 0049977 or PCT patent application No. WO 82/01368. The preparation of two novel alcohols are described infra.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combt flies, mosquitoes and beetles.

Certain of the compounds of formula I possess an excellent lethal power and a very good knock-down power and the products of Examples 1 to 8, 12 and 14 are particularly remarkable on this point. The products of formula I have the advantages of being very photostable and not being toxic to mammals. The various properties of the compounds of formula I correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

The invention also includes compositions intended to combat parasites of warm-blooded animals, parasites of premises and parasites of vegetables containing at least one compound of formula I.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of the invention in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzyl (piperonyl butoxide) or N-(2-ethylheptyl)-bicyclo-[2,2-1]5-heptene-2,3-dicarboximide or piperonyl-bis-2-(2'-n-butoxy-ethoxy)-ethyl acetal (tropital).

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals. sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

Another feature of the invention are insecticidal, acaricidal or nematocidal associations containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furyl-methyl alcohol, of 3-phenoxy-benzyl alcohol and α-cyano-3- phenoxy-benzyl alcohols with chrysanthemic acids, esters of 5-benzyl-3-furyl-methyl alcohol with 2,2-dimethyl-3-(2-oxo-3-tetrahydrothiophenylidene-methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimido-methyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of least one compound of formula I.

Also part of the invention are the two new alcohols of formula III, namely 2-(pyrrol-1-yl)-6-pyridylmethanol and (R,S)α-cyano-2-methyl-3-(pyrrol-1-yl)-benzyl alcohol.

In the following examples, there are described several preferred embodiments to illustrate the invention. However, it is to be understood that the invention is not intended to be limited to the specific embodiments.

EXAMPLE 1

2-methyl-3-(pyrrol-1-yl)-benzyl (1R,cis,ΔZ)2,2-dimethyl-3-[3-methoxy-3-oxo-1-propenyl]-cyclopropane-carboxylate.

0.5% by weight with respect to acid of 4-dimethylamino-pyridine was added under nitrogen with stirring at 0° to 5° C. to a mixture of 11 mmoles of (1R,cis,ΔZ) 2,2-dimethyl-3-[3-methoxy-3-oxo-1-propenyl]-cyclopropane-carboxylic acid, 10 mmoles of 2-methyl-3-(pyrrol-1-yl)-benzyl alcohol, 11 mmoles of dicyclohexylcarbodiimide and 20 volumes of methylene chloride and the mixture was stirred under nitrogen until the temperature had returned to room temperature or about 4 hours. The mixture was vacuum filtered and the filter was rinsed with methylene chloride. The filtrate was evaporated to dryness under reduced pressure and the residue was chromatographed over silica gel. Elution with an 8-2 hexaneisopropyl ether mixture yielded an 83% yield of 2-methyl-3-(pyrrol-1-yl)-benzyl (1R,cis,ΔZ) 2,2-dimethyl-3-[3-methoxy-3-oxo-1-propenyl]-cyclopropane-carboxylate with a specific rotation of $[\alpha]_D^{20} = +47°$ (c=0.6% in chloroform).

EXAMPLES 2 to 20

Using the procedure of Example 1, the appropriate acid and alcohols, which are described in the literature or prepared infra, were reacted to obtain the corresponding compounds of formula I.

2—2-methyl-3-phenyl-benzyl (1R,cis,ΔZ) 2,2-dimethyl-3-[3-methoxy-3-oxo-1-propenyl]-cyclopropane-carboxylate 3—2-methyl-3-(pyrrol-1-yl)-benzyl (1R,cis,ΔZ) 2,2-dimethyl-3-[3-tert.-butoxy-3-oxo-1-propenyl]-cyclopropane-carboxylate 4—2-methyl-3-phenyl-benzyl (1R,cis,ΔZ) 2,2-dimethyl-3-[3-tert.-butoxy-3-oxo-1-propenyl]-cyclopropanecarboxylate 5—2-methyl-3-(pyrrol-1-yl)-benzyl (1R,cis,ΔE)2,2-dimethyl-3-[3-ethoxy-3-oxo-2-fluoro-1-propenyl]-cyclopropanecarboxylate 6—2-methyl-3-phenyl-benzyl (1R,cis,ΔE) 2,2-dimethyl-3-[3-ethoxy-3-oxo-2-fluoro-1-propenyl]-cyclopropanecarboxylate 7—2-methyl-3-phenyl-benzyl (1R,cis,ΔE) 2,2-dimethyl-3-[3-tert.-butoxy-3-oxo-2-fluoro-1-propenyl]-cyclopropane-carboxylate 8—2-methyl-3-(pyrrol-1-yl)-benzyl (1R,cis,ΔE) 2,2-dimethyl-3-[3-tert.-butoxy-3-oxo-2-fluoro-1-propenyl]cyclopropane-carboxylate 9—2-methyl-3-(2,5-dimethyl-pyrrol-1-yl)-benzyl (1R,cis,ΔE) 2,2-dimethyl-3-[3-ethoxy-3-oxo-2-fluoro-1-propenyl]cyclopropane-carboxylate 10—2-methyl-3-(2,5-dimethyl-pyrrol-1-yl)-benzyl (1R,cis,ΔZ) 2,2-dimethyl-3-[3-tert.butoxy-3-oxo-1-propenyl]-cyclopropane-carboxylate 11—2-methyl-3-(2,5-dimethyl-pyrrol-1-yl)-benzyl (1R,cis,ΔZ) 2,2-dimethyl-3-[3-methoxy-3-oxo-1-propenyl]cyclopropane-carboxylate 12—3-(pyrrol-1-yl)-benzyl (1R,cis,ΔZ) 2,2-dimethyl-3-[3-methoxy-3-oxo-1-propenyl]-cyclopropane-carboxylate 13—3-(pyrrol-1-yl)-benzyl (1R,cis,ΔZ) 2,2-dimethyl-3-[3-tert.butoxy-3-oxo-1-propenyl]-cyclopropane-carboxylate 14—4-methyl-3-(pyrrol-1-yl)-benzyl (1R,cis,ΔZ) 2,2-dimethyl-3-[3-methoxy-3-oxo-1-propenyl]-cyclopropanecarboxylate 15—4-methyl-3-(pyrrol-1-yl)-benzyl (1R,cis,ΔZ) 2,2-dimethyl-3-[3-tert.-butoxy-3-oxo-1-propenyl]-cyclopropane-carboxylate 16—2,4-dimethyl-3-(pyrrol-1-yl)-benzyl (1R,cis,ΔZ) 2,2-dimethyl-3-[3-methoxy-3-oxo-1-propenyl]-cyclopropanecarboxylate 17—2,4-dimethyl-3-(pyrrol-1-yl)-benzyl (1R,cis,ΔZ) 2,2-dimethyl-3-[3-tert.-butoxy-3-oxo-1-propenyl]-cyclopropane-carboxylate 18—[6-(pyrrol-1-yl)-2-pyridyl]-methyl (1R,cis,ΔZ) 2,2-dimethyl-3-[3-tert.-butoxy-3-oxo-1-propenyl]-cyclopropane-carboxylate 19—[6-(pyrrol-1-yl)-2-pyridyl]-methyl (1R,cis,ΔZ) 2,2-dimethyl-3-[3-methoxy-3-oxo-1-propenyl]-cyclopropanecarboxylate 20—(R) and (S)-cyano-2-methyl-3-(pyrrol-1-yl)-benzyl (1R,cis,ΔZ) 2,2-dimethyl-3-[3-tert.-butoxy-3-oxo-1-propenyl]cyclopropane-carboxylate.

The principal operating conditions and the melting points and specific rotations of the products are reported in the following Table.

|  | Y | Z | R₁ | Ar | Reaction time | Yield | $a_D(CHCl_3)$ | Chromatography solvent |
|---|---|---|---|---|---|---|---|---|
| Example 1 | H | O | CH₃ | -CH₂-(2-methyl-3-pyrrolyl-phenyl) | 4 h | 83% | +47° c = 0,6% | hexane isopropyl ether (8-2) |
| Example 2 | H | O | CH₃ | -CH₂-(2-methyl-biphenyl) | 20 h | 85% | +39° c = 0,5% | hexane isopropyl ether (9-1) |
| Example 3 | H | O | -C(CH₃)₃ | -CH₂-(2-methyl-3-pyrrolyl-phenyl) | 5 h | 88% | +50° c = 0,55% | hexane isopropyl ether (9-1) |
| Example 4 | H | O | -C(CH₃)₃ | -CH₂-(2-methyl-biphenyl) | 5 h | 86% | +46,5° c = 0,3% | hexane isopropyl ether (9-1) |
| Example 5 | F | O | C₂H₅ | -CH₂-(2-methyl-3-pyrrolyl-phenyl) | 1 h 45 | 82% | +20° c = 0,5% | hexane isopropyl ether (85-15) |
| Example 6 | F | O | C₂H₅ | -CH₂-(2-methyl-biphenyl) | 3 h | 78% | +16,5° c = 0,5% | hexane isopropyl ether (8-2) |
| Example 7 | F | O | -C(CH₃)₃ | -CH₂-(2-methyl-biphenyl) | 17 H | 85% | +25° ± 2° c = 0,4% | hexane isopropyl ether (9-1) |
| Example 8 | F | O | -C(CH₃)₃ | -CH₂-(2-methyl-3-pyrrolyl-phenyl) | 17 H | 89% | +30,5° ± 2° c = 0,5% | hexane isopropyl ether (9-1) |

-continued

| | Y | Z | R₁ | Ar | Reaction time | Yield | α_D(CHCl₃) | Chromatography solvent |
|---|---|---|---|---|---|---|---|---|
| Example 9 | F | O | —C₂H₅ | —CH₂— (2,6-dimethylphenyl with N-(2-methylpyrrol-1-yl)) | 2 H | 68% | +26° ± 2°<br>c = 0,5% | hexane<br>isopropyl ether<br>(7-3) |
| Example 10 | H | O | —C(CH₃)₃ | —CH₂— (2,6-dimethylphenyl with N-(2-methylpyrrol-1-yl)) | 15 H | 77% | +49,5 ± 2,5°<br>c = 0,5% | hexane<br>ethyl acetate<br>(9-1) |
| Example 11 | H | O | CH₃ | —CH₂— (2,6-dimethylphenyl with N-(2-methylpyrrol-1-yl)) | 16 H | 83% | +54,5° ± 2,5°<br>c = 0,5% | hexane<br>ethyl acetate<br>(9,5-0,5) |
| Example 12 | H | O | CH₃ | —CH₂— (3-pyrrol-1-yl-phenyl) | 18 H | 78% | +51,0° ± 1,5°<br>c = 0,8% | hexane<br>ethyl acetate<br>(8-2) |
| Example 13 | H | O | —C(CH₃)₃ | —CH₂— (3-pyrrol-1-yl-phenyl) | 18 H | 66% | +58,5° ± 1,5°<br>c = 1%<br>F = 82° C. | hexane<br>ethyl acetate<br>(9-1) |
| Example 14 | H | O | CH₃ | —CH₂— (4-methyl-3-pyrrol-1-yl-phenyl) | 3 H | 90% | +44° ± 2°<br>c = 0,5% | hexane<br>ethyl acetate<br>(9-1) |

-continued

| | Y | Z | R₁ | Ar | Reaction time | Yield | $\alpha_D$(CHCl₃) | Chromatography solvent |
|---|---|---|---|---|---|---|---|---|
| Example 15 | H | O | —C(CH₃)₃ | —CH₂—(2-methyl-3-(pyrrol-1-yl)phenyl) | 3 H | 82% | +48° ± 2°<br>c = 0,5% | hexane<br>ethyl acetate<br>(9-1) |
| Example 16 | H | O | CH₃ | —CH₂—(2,6-dimethyl-3-(pyrrol-1-yl)phenyl) | 2 H | 62% | +37° ± 2°<br>c = 0,5% | hexane<br>ethyl acetate<br>(9-1) |
| Example 17 | H | O | —C(CH₃)₃ | —CH₂—(2,6-dimethyl-3-(pyrrol-1-yl)phenyl) | 2 H | 86% | +42,5° ± 2°<br>c = 0,5% | hexane<br>ethyl acetate<br>(9-1) |
| Example 18 | H | O | —C(CH₃)₃ | —CH₂—(6-(pyrrol-1-yl)pyridin-2-yl) | 1 H 30 | 79% | +99,5° ± 0,5°<br>c = 0,5% | hexane<br>ethyl acetate<br>(8-2) |
| Example 19 | H | O | CH₃ | —CH₂—(6-(pyrrol-1-yl)pyridin-2-yl) | 1 H 30 | 61% | +87,5° ± 1,5°<br>c = 1%<br>F = 80° C. | hexane<br>ethyl acetate<br>(8-2) |
| Example 20 | H | O | —C(CH₃)₃ | —CH(CN)—(2-methyl-3-(pyrrol-1-yl)phenyl)<br>(R and S) | 15 H | 22%<br>(R or S isomer)<br>9,3%<br>(S or R isomer) | Analyse:<br>C₂₆H₃₀N₂O₄<br>calculated<br>C % 71,87<br>H % 6,96<br>N % 6,45<br>Found:<br>C % 72,0<br>H % 7,1<br>N % 6,3 | hexane<br>isopropyl ether<br>(7-3) |

PREPARATION A (R,S)α-cyano-2-methyl-3-(pyrrol-1-yl)-benzyl alcohol

STEP A: 3-(pyrrol-1-yl)-2-methyl-benzaldehyde

A suspension of 6 g of (3-pyrrol-1-yl)2-methylbenzyl alcohol, 300 ml of benzene and 30 g of manganese dioxide was stirred at room temperature for 3 hours and 12 g of manganese dioxide were added thereto. After stirring for 2 hours, another 6 g of manganese dioxide were added to the mixture which was then stirred at room temperature for 19 hours and was vacuum filtered. The filter was rinsed with benzene and the filtrate was evaporated to dryness under reduced pressure to obtain 4.89 g of 3-(pyrrol-1-yl)-2-methylbenzaldehyde melting at 82° C.

STEP B: (R,S)α-cyano-2-methyl-3-(pyrrol-1-yl)-benzyl alcohol 4 ml of acetic acid dropwise and then 1.4 g of sodium cyanide were added at 10° C. to a solution of 4.89 g of the product of Step A, 50 ml of methanol and 20 ml of water and the mixture was stirred at 10° C. for 5 hours and was poured into 60 ml of ice water. The mixture was stirred for one hour and the decanted aqueous phase was extracted with methylene chloride. The organic phase was dried and evaporated to dryness under reduced pressure. The residue was chromatographed over silica gel and was eluted with an 8-2 hexane-ethyl acetate mixture to obtain 3.59 g of (R,S)α-cyano-2-methyl-3-(pyrrol-1-yl)-benzyl alcohol.

NMR Spectrum (deuterochloroform): Peaks at 5.78 ppm (hydrogen on carbon attached to —CN); at 2.23 ppm (hydrogens of 2-methyl of benzyl).

PREPARATION B

2-(pyrrol-1-yl)-6-pyridyl-methanol

STEP A: 6-acetamido-2-methyl-pyridine

A mixture of 50 g of 6-amino-2-methyl-pyridine in 250 ml of acetic acid anhydride was refluxed for one hour and was then evaporated to dryness under reduced pressure. The residue was taken up in methylene chloride and the solution was washed with water and then with aqueous sodium hydroxide solution and then with water. The solution was dried and evaporated to dryness under reduced pressure. The residual oil was crystallized from isopropyl ether to obtain 41 g of 6-acetamido-2-methyl-pyridine melting at 87° C.

STEP B: 6-acetamido-picolinic acid 100 g of potassium permanganate were added over two hours at 70° C. to a mixture of 40 g of the product of Step A in 400 ml of water and the mixture was stirred at 70° to 80° C. for one hour and was filtered. The filtrate was concentrated under reduced pressure to a small volume and was cooled to 10°-15° C. The mixture was filtered and the aqueous phase was acidified with 2N hydrochloric acid. The mixture was vacuum filtered and the crystalline product was empasted with ethanol and then with ether. The product was dried under reduced pressure and was crystallized from ethanol to obtain 16 g of 6-acetamido-picolinic acid melting at 212° C.

STEP C: 2-amino-6-methoxy carbonyl-pyridine

Gaseous hydrogen chloride was bubbled at room temperature for one hour through a solution formed by addition of 15 g of the product of Step B to 150 ml of methanol at 5° C. and the mixture was refluxed for 4 hours and cooled to room temperature. The mixture was stirred for 16 hours and was evaporated under reduced pressure. The residue was taken up in 50 ml of water and the solution was filtered. The filtrate was made alkaline by addition of concentrated ammonium hydroxide and was extracted with chloroform. The organic phase was dried and evaporated to dryness under reduced pressure to obtain 9.54 g of 2-amino-6-methoxy carbonyl-pyridine melting at 87° C.

STEP D: 2-(pyrrol-1-yl)-6-methoxy carbonyl-pyridine 6.3 ml of 2,5-dimethoxy-tetrahydrofuran were added with stirring at room temperature to a solution of 7 g of the product of Step C in 17.5 ml of acetic acid and was refluxed for one hour. Acetic acid was evaporated under reduced pressure and the oil residue was chromatographed over silica gel. Elution with methylene chloride yielded 3.7 g of 2-(pyrrol-1-yl)-6-methoxy carbonyl-pyridine melting at 61° C.

STEP E: 2-(pyrrol-1-yl)-6-pyridyl-methanol 38 ml of diisobutyl aluminum were added dropwise over one hour at −40° C. to a solution of 3.7 g of the product of Step D in 40 ml of toluene and the mixture was stirred at −30° C. for 30 minutes. 110 ml of an aqueous molar solution of double sodium potassium tartarate were slowly added to the mixture while keeping the temperature below 10° C. and the mixture was stirred for 16 hours at room temperature. The decanted organic phase was dried and evaporated to dryness under reduced pressure to obtain 2.9 g of 2-(pyrrol-1-yl)-6-pyridyl-methanol melting at 55° C.

EXAMPLE 21

A soluble concentrate was prepared by homogenously mixing 0.25 g of the product of Example 1, 1 g of piperonyl butoxide, 0.25 g of Tween 80, 0.1 g of Topanol A and 98.4 g of water.

An emulsifiable concentrate was prepared by intimately mixing 0.015 g of the product of Example 2, 0.5 g of piperonyl butoxide, 0.1 g of Topanol A, 3.5 g of Tween 80 and 95.885 g of xylene.

A second emulsifiable concentrate was prepared by homogeneously mixing of 1.5 g of the product of Example 3, 20 g of Tween 80, 0.1 g of Topanol A and 78.4 g of xylene.

TEST DATA

A. Lethal activity against houseflies

The test insects were 4 to 5 days old female houseflies of a strain sensitive to pyrethinoids, bred at 22°-23° C. and 60 to 65% relative humidity. The test was effected by topical application of 1 μl of an acetone solution of the test compound on the dorsal thorax of the insects with an Arnold micromanipulator. 50 insects were used for each dose and the readings of number of dead flies was taken 24 hours after treatment to determine the $DL_{50}$ or dose in nanograms necessary to kill 50% of the insects. The $DL_{50}$ for the compounds of Examples 5 and 6 was 12 and 5.1 in ng per insect, respectively.

B. Lethal activity against Spodoptera Littoralis Larvae

The test was effected by topical application with an Arnold micromanipulator of an acetone solution of the test compound to the dorsal thorax of 15 larvae for each test which were in the fourth stage of larvae development or about 10 days old at 24° C. and 65% relative humidity. After treatment, the larvae were placed in artificial nutritive media (Poitout medium) and the $DL_{50}$ in nanograms per larva were determined 48 hours later. The $DL_{50}$ for the compounds of Examples 1 and 2 was 6.9 and 7.1 in ng per larva respectively indicated a good lethal activity.

C. Knock-down effect on houseflies 4 to 5 day old female houseflies were directly sprayed in a Kearns and March chamber at a concentration of 0.25 g/l in a mixture of Isopar L (petroleum solvent) containing 5% acetone using 2 ml in one second. 50 insects were used for each test and reading were taken each minute for 10 minutes and then at 15 minutes to determine the $KT_{50}$ in minutes by the known method. The $KT_{50}$ for the compounds of Examples 1, 2, 5, 12 and 14 was 3.54, 4.1, 3.54, 3.19 and 3.16 minutes, respectively, indicating a good activity.

D. Lethal activity against Acanthocephalus Obtectus larvae

The test was effected by topical application to Acanthocephalus Obtectus larvae in the second last stage of development similar to the procedure of Test B and after treatment, the larvae were fed bean plants. The number of dead was determined 72 hours after treatment and the product of Example 6 had a $DL_{50}$ of 12.1 ng per insect showing a good lethal activity.

E. Acaricidal Activity against Tetranychus urticae

Bean plants containing 2 leaves were treated with a Fisher pistol with 4 ml of a toxic solution per plant in a 1—1 water-acetone mixture and were allowed to dry for 12 hours. Then the plants were infested with 25 female Tetranychus urticae per leaf and were then placed under a ventilated cover at 22°-23° C. and a relative humidity of 60-65% with a constant artificial light. The reading of dead insects was taken after 24 and 48 hours to determine the $CL_{50}$ in mg/hl. The $CL_{50}$ for the compounds of Examples 3, 4, 7 and 8 was 419, 476, 399 and 661, respectively.

Various modifications of the compounds and methods of the invention may be made without departing from the spirit or scope thereof and it is to be understood that the invention is intended to be limited only as defined in the appended claims.

What we claim is:

1. An ester in any possible isomeric form or a mixture thereof having the formula

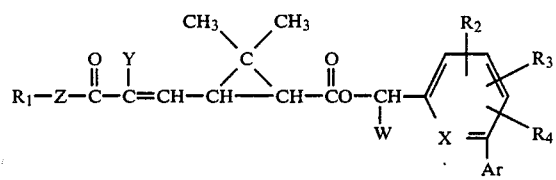

wherein Y is selected from the group consisting of hydrogen and halogen, Z is selected from the group consisting of —O— and —S—, $R_1$ is alkyl of 1 to 8 carbon atoms, $R_2$, $R_3$ and $R_4$ are individually selected from the group consisting of hydrogen, halogen, alkyl of 1 to 8 carbon atoms, haloalkyl of 1 to 8 carbon atoms containing 1 to 3 halogens and alkoxy of 1 to 8 carbon atoms, W is selected from the group consisting of hydrogen and —CN, X is selected from the group consisting of =CH— or =N—, Ar is selected from the group consisting of phenyl, naphthyl and pyrrol-1-yl and the ethylenic double bond may have Z or E geometry.

2. A compound of claim 1 wherein Y is selected from the group consisting of hydrogen or halogen, $R_2$, $R_3$ and $R_4$ are the same, W is hydrogen and X is =CH—.

3. A compound of claim 1 wherein the cyclopropane ring has the 1R,cis structure.

4. A compound of claim 1 wherein Ar is pyrrolyl.

5. A compound of claim 1 wherein Ar is phenyl.

6. A compound of claim 1 wherein $R_2$, $R_3$ and $R_4$ are alkyl of 1 to 4 carbon atoms.

7. A compound of claim 6 wherein at least one of $R_2$, $R_3$ or $R_4$ is methyl.

8. A compound of claim 1 wherein $R_3$ and $R_4$ are hydrogen.

9. A compound of claim 1 wherein Y is hydrogen.

10. A compound of claim 1 wherein Y is fluorine.

11. A compound of claim 1 wherein Z is oxygen.

12. A compound of claim 1 having the formula

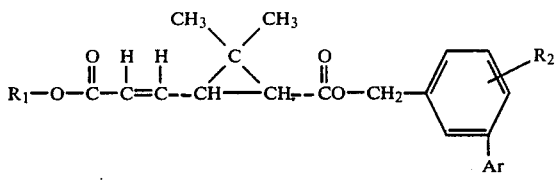

wherein $R_1$, $R_2$ and Ar have the definition of claim 1, the double bond has Z geometry and the cyclopropane group has 1R, cis structure.

13. A compound of claim 1 selected from the group consisting of 2-methyl-3-(pyrrol-1-yl)-benzyl (1R,cis,ΔZ) 2,2-dimethyl-3-[3-methoxy-3-oxo-1-propenyl]-cyclopropane-carboxylate, 2-methyl-3-phenyl-benzyl (1R,cis,ΔZ) 2,2-dimethyl-3-[3-methoxy-3-oxo-1-propenyl]-cyclopropane-carboxylate, 2-methyl-3-(pyrrol-1-yl)-benzyl (1R,cis,ΔZ) 2,2-dimethyl-3-[3-tert.-butoxy-3-oxo-1-propenyl]-cyclopropane-carboxylate, 2-methyl-3-phenylbenzyl (1R,cis,ΔZ) 2,2-dimethyl-3-[3-tert.-butoxy-3-oxo-1-propenyl]-cyclopropane-carboxylate, 2-methyl-3-(pyrrol-1-yl)benzyl (1R,cis,ΔE) 2,2-dimethyl-3-[3-ethoxy-3-oxo-2-fluoro-1-propenyl]-cyclopropane-carboxylate, 2-methyl-3-phenyl-benzyl (1R,cis,ΔE) 2,2-dimethyl-3-[3-ethoxy-3-oxo-2-fluoro-1-propenyl]cyclopropane-carboxylate, 2-methyl-3-phenyl-benzyl (1R,cis,ΔE) 2,2-dimethyl-3-[3-tert.-butoxy-3-oxo-2-fluoro-1-propenyl]cyclopropane-carboxylate, 2-methyl-3-(pyrrol-1-yl)-benzyl (1R,cis,ΔE) 2,2-dimethyl-3-[3-tert.-butoxy-3-oxo-2-fluoro-1-propenyl]-cyclopropane-carboxylate, 3-(pyrrol-1-yl)-benzyl (1R,cis,ΔZ) 2,2-dimethyl-3-[3-methoxy-3-oxo-1-propenyl]-cyclopropane-carboxylate and 4-methyl-3-(pyrrol-1-yl)-benzyl (1R,cis,ΔZ) 2,2-dimethyl-3-[3-methoxy-3-oxo-1-propenyl]-cyclopropane-carboxylate.

14. An insecticidal composition comprising an insecticidally effective amount of an ester in any possible isomeric form or a mixture thereof having the formula

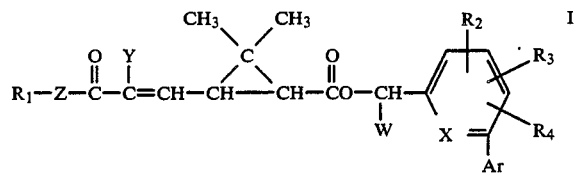

wherein Y is selected from the group consisting of hydrogen and halogen, Z is selected from the group consisting of —O— and —S—, $R_1$ is alkyl of 1 to 8 carbon atoms $R_2$, $R_3$ and $R_4$ are individually selected from the group consisting of hydrogen, halogen, alkyl of 1 to 18 carbon atoms, haloalkyl of 1 to 8 carbon atoms containing 1 to 3 halogens and alkoxy of 1 to 8 carbon atoms, W is selected from the group consisting of hydrogen and —CN, X is selected from the group consisting of =CH— or =N—, Ar is selected from the group consisting of phenyl, naphthyl or pyrrolyl and the enthylenic double bond may have Z or E geometry in combination with an inert carrier.

15. A composition of claim 14 wherein Y is selected from the grouop consisting of hydrogen or halogen, $R_2$, $R_3$ and $R_4$ are the same, W is hydrogen and X is =CH.

16. A composition of claim 14 wherein the cyclopropane ring has the 1R,cis structure.

17. A composition of claim 14 wherein Ar is pyrrol-1-yl.

18. A composition of claim 14 wherein Ar is phenyl.

19. A composition of claim 14 wherein $R_2$, $R_3$ and $R_4$ are alkyl of 1 to 4 carbon atoms.

20. A composition of claim 20 wherein one of $R_2$, $R_3$ or $R_4$ is methyl.

21. A composition of claim 14 wherein $R_3$ and $R_4$ are hydrogen.

22. A composition of claim 14 wherein Y is hydrogen.

23. A composition of claim 14 wherein Y is fluorine.

24. A composition of claim 14 wherein Z is oxygen.

25. A composition of claim 14 having the formula

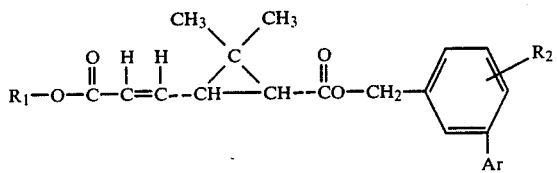

wherein $R_1$, $R_2$ and Ar have the definition of claim 1, the double bond has Z geometry and the cyclopropane group has 1R,cis structure.

26. A method of combatting insects comprising contacting insects with an insectionally effective amount of an ester in any possible isomeric form or a mixture thereof having the formula

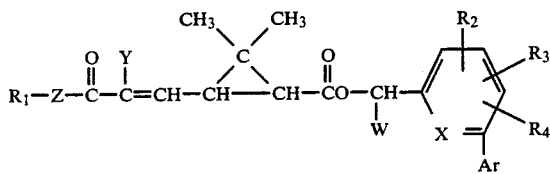

wherein Y is selected from the group consisting of hydrogen and halogen, Z is selected from the group consisting of —O— and —S—, $R_1$ is alkyl of 1 to 8 carbon atoms $R_2$, $R_3$ and $R_4$ are individually selected from the group consisting of hydrogen, halogen, alkyl of 1 to 18 carbon atoms, haloalkyl of 1 to 8 carbon atoms containing 1 to 3 halogens and alkoxy of 1 to 8 carbon atoms, W is selected from the group consisting of hydrogen and —CN, X is selected from the group consisting of =CH— or —N—, Ar is selected from the group consisting of phenyl, naphthyl and pyrrol-1-yl and the enthylenic double bond may have Z or E geometry in combination with an inert carrier.

27. A method of claim 26 wherein Y is selected from the group consisting of hydrogen or halogen, $R_2$, $R_3$ and $R_4$ are the same, W is hydrogen and X is =CH—.

28. A method of claim 26 wherein the cyclopropane ring has the 1R,cis structure.

29. A method of claim 26 wherein Ar is pyrrol-1-yl.

30. A method of claim 26 wherein Ar is phenyl.

31. A method of claim 26 wherein $R_2$, $R_3$ and $R_4$ are alkyl of 1 to 4 carbon atoms.

32. A method of claim 31 wherein one of $R_2$, $R_3$ or $R_4$ is methyl.

33. A method of claim 26 wherein $R_3$ and $R_4$ are hydrogen.

34. A method of claim 26 wherein Y is hydrogen.

35. A method of claim 26 wherein Y is fluorine.

36. A method of claim 26 wherein Z is oxygen.

37. A method of claim 26 having the formula

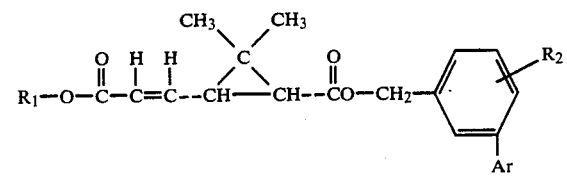

wherein $R_1$, $R_2$ and Ar have the definition of claim 1, the double bond has Z geometry and the cyclopropane group has 1R,cis structure.

* * * * *